United States Patent [19]

Cantor

[11] Patent Number: 5,633,003
[45] Date of Patent: May 27, 1997

[54] USE OF INTRATRACHEALLY ADMINISTERED HYALURONIC ACID TO AMELIORATE EMPHYSEMA

[76] Inventor: Jerome O. Cantor, 5900 Arlington Ave., Apt. 4H, Riverdale, N.Y. 10471

[21] Appl. No.: 221,866

[22] Filed: Mar. 31, 1994

[51] Int. Cl.$^6$ .................... A61K 31/715; A01N 43/04
[52] U.S. Cl. ................... 424/434; 424/435; 514/54
[58] Field of Search .................. 424/422, 423, 424/78.05, 434, 435; 514/54, 826

[56] References Cited

U.S. PATENT DOCUMENTS

| | | | |
|---|---|---|---|
| 4,119,096 | 10/1978 | Drews | 128/194 |
| 4,649,911 | 3/1987 | Knight et al. | 128/200.21 |
| 4,725,585 | 2/1988 | Wenge et al. | 514/54 |
| 4,851,521 | 7/1989 | de Valle et al. | 514/54 |
| 4,925,678 | 5/1990 | Ranney | 424/493 |
| 5,043,165 | 8/1991 | Radhakrishnan | 424/450 |
| 5,049,388 | 9/1991 | Knight et al. | 424/450 |
| 5,108,759 | 4/1992 | Ranney | 424/493 |
| 5,116,616 | 5/1992 | Gonenne | 424/94.4 |
| 5,154,841 | 10/1992 | Cullis-Hill et al. | 514/54 |
| 5,162,307 | 11/1992 | Digenis et al. | 514/19 |

OTHER PUBLICATIONS

Karlinsky, J.B. (Apr. 1978) "Glycosaminoglycans: Amounts and distribution in Experimental Pulmonary Fibrosis and Emphysema", Am. Rev. Resp. Dis. 117:356 (Exhibit 9).

Konno, K., et al. (Nov. 1982) "A Biochemical Study on Glycosaminoglycans (Mucopolysaccharides in Emphysematous and in Aged Lungs", Am. Rev. Resp. Dis. 126:797–801 (Exhibit 10).

Lafuma, C., et al. (1985) "Biosynthesis of Hyaluronic Acid, Heparan Sulfate and Structural Glycoproteins in Hamster Lung Explants During Elastase Induse Emphysema", Conn. Tiss. Res. 13:169–179 (Exhibit 11).

McDevitt, C.A., et al. (1989) "Cigarette Smoke Degrades Hyaluronic Acid", Lung 167:237–245 (Exhibit 12).

Pecora, L.J., et al. (1965) "Biochemical Study of Ground Substance in Normal and Emphysematous Lungs", Am. Rev. Resp. Dis. 95:623–861 (Exhibit 13).

Primary Examiner—Carlos Azpuru
Attorney, Agent, or Firm—John P. White

[57] ABSTRACT

The subject invention is directed to the treatment of respiratory disorders by intratracheal administration of an effective amount of hyaluronic acid. Respiratory disorders include emphysema, chronic bronchitis, asthma, pulmonary edema, acute respiratory distress syndrome, bronchopulmonary dysplasia, pulmonary fibrosis, and pulmonary atelectasis. The treatment is intended for a variety of mammals, such as premature neonates to adult humans. Administration of hyaluronic acid may be performed by aerosol, which can be generated by a nebulizer, or by instillation. The hyaluronic acid may be administered alone, or with a carrier such as saline solution, DMSO, an alcohol or water. It may be isolated from a natural source such as a bovine or rooster. The effective daily amount of hyaluronic acid is from about 10 µg/kg to about 1 mg/kg of body weight.

14 Claims, 5 Drawing Sheets

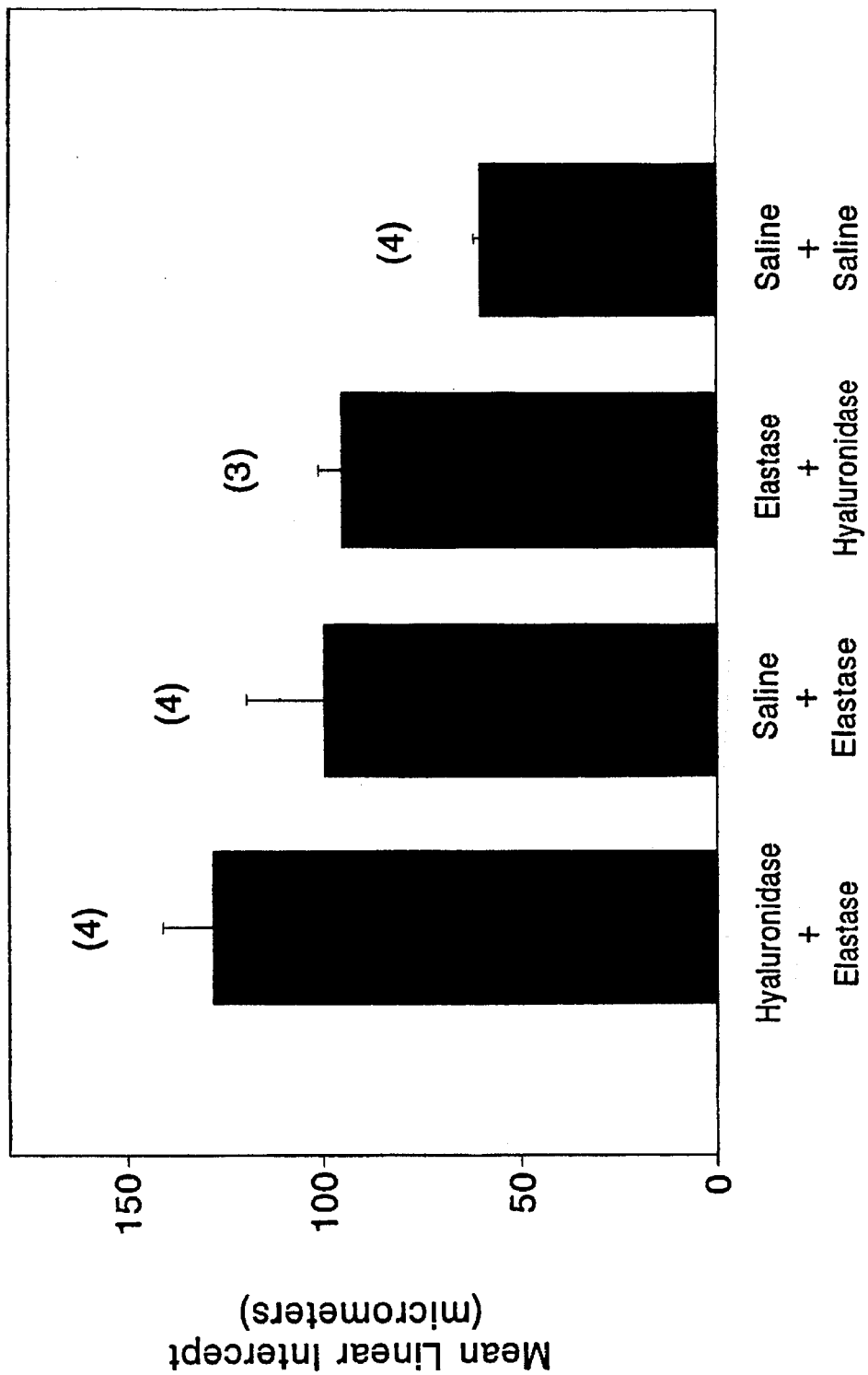

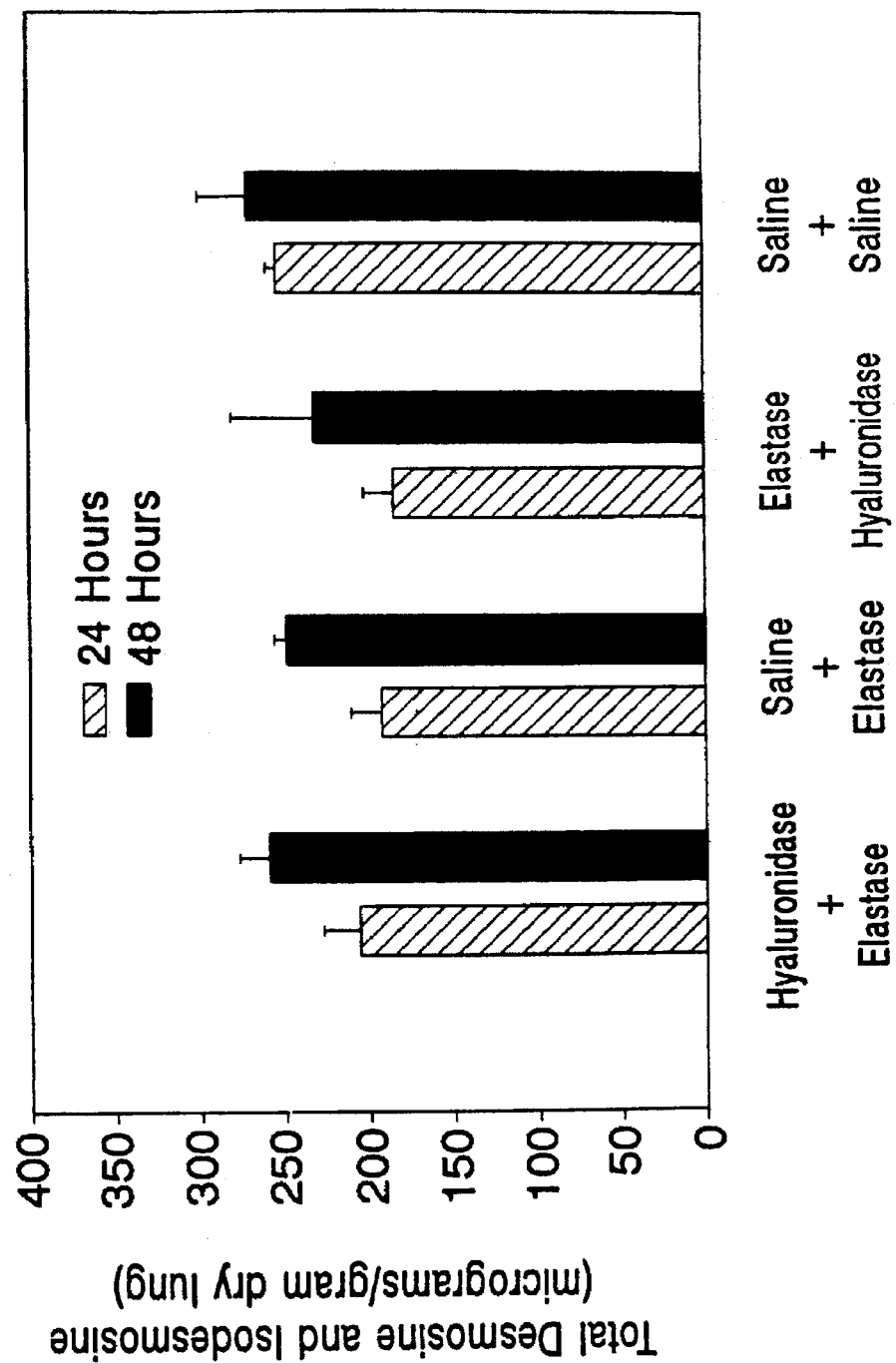

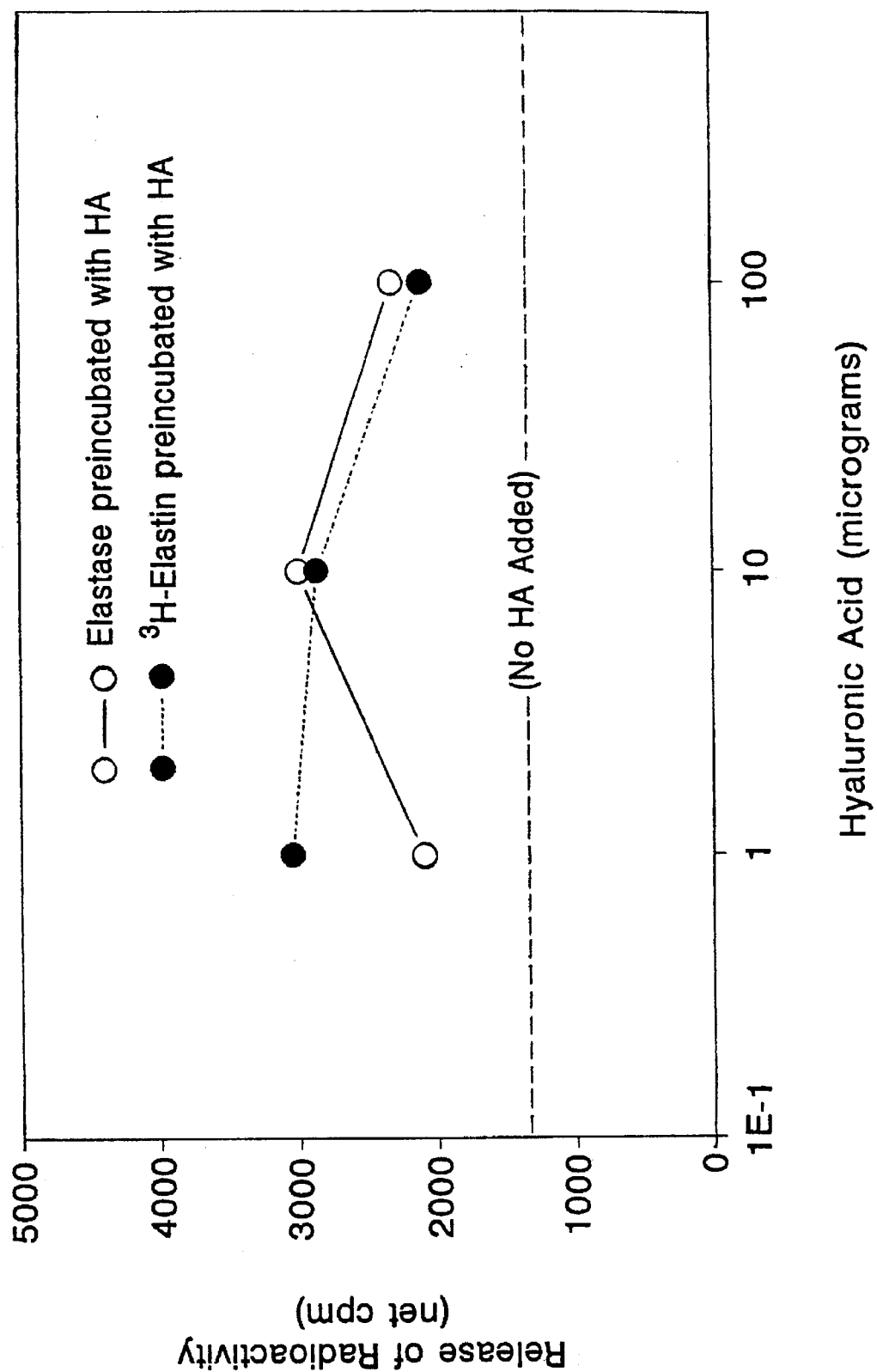

USE OF INTRATRACHEALLY ADMINISTERED HYALURONIC ACID TO AMELIORATE EMPHYSEMA

BACKGROUND OF THE INVENTION

Throughout this application various publications are referenced by numbers. The full citations are listed at the end of the specification immediately preceeding the claims.

The proteinase-antiproteinase concept of emphysema has served to focus research on the role of elastases, with the hope that inhibiting the activity of these enzymes will prevent lung injury (1–4). Such a treatment strategy assumes, however, that emphysema is caused by a specific type of biochemical derangement, as in the case of alpha-1-antiproteinase deficiency (5). If the disease represents a more general response of the lung to a variety of insults (with elastases playing a variable role), then enzyme inhibition may have only limited efficacy.

In attempting to address the issue of whether emphysema is a specific or multifactorial disease process, a series of experiments were previously performed by this laboratory involving both the induction and modification of experimental emphysema with agents other than elastases. It was found that elastase-induced emphysema is greatly enhanced by exposing the lungs to a normally nontoxic concentration of oxygen (60 percent) (6). Similarly, it was possible to produce air-space enlargement with a nonelastolytic enzyme, hyaluronidase, by the addition of 60 percent oxygen (7). The experiments using hyaluronidase and 60 percent oxygen showed that loss of lung elastin occurred only when both agents were given concomitantly, suggesting the possibility that hyaluronidase may facilitate the breakdown of elastic fibers by making them more accessible to injury.

This hypothesis was further tested in the current studies. To test this invention, hamsters were given intratracheal instillments of hyaluronidase, followed by elastase, and then examined for air-space enlargement. The findings indicate that pretreatment with hyaluronidase enhances elastase-induced emphysema. Furthermore, it was found that intratracheally administered hyaluronic acid had the opposite effect (despite its inability to directly inhibiting elastase). These results provide additional evidence that air-space enlargement is a complex phenomenon and that new approaches to the treatment of emphysema may be required.

SUMMARY OF THE INVENTION

The subject invention is directed to the treatment of respiratory disorders by intratracheal administration of an effective amount of hyaluronic acid. Respiratory disorders include emphysema, chronic bronchitis, asthma, pulmonary edema, acute respiratory distress syndrome, bronchopulmonary dysplasia, pulmonary fibrosis, and pulmonary atelectasis. The treatment is intended for a variety of mammals, such as premature neonates to adult humans.

Administration of hyaluronic acid may be performed by aerosol, which can be generated by a nebulizer, or by instillation. The hyaluronic acid may be administered alone, or with a carrier such as saline solution, DMSO, an alcohol or water. It may be isolated from a natural source such as a cow or rooster or prepared by fermentation. The effective daily amount of hyaluronic acid is from about 10 µg/kg to about 1 mg/kg of body weight.

BRIEF DESCRIPTION OF THE FIGURES

FIG. 1:

Pre-treatment of the lung with hyaluronidase significantly increased elastase-induced air-space enlargement (p<0.05). Reversing the order of enzyme administration abolished this effect. Measurements were made 1 week following completion of the enzyme instillments.

Figure 2B:
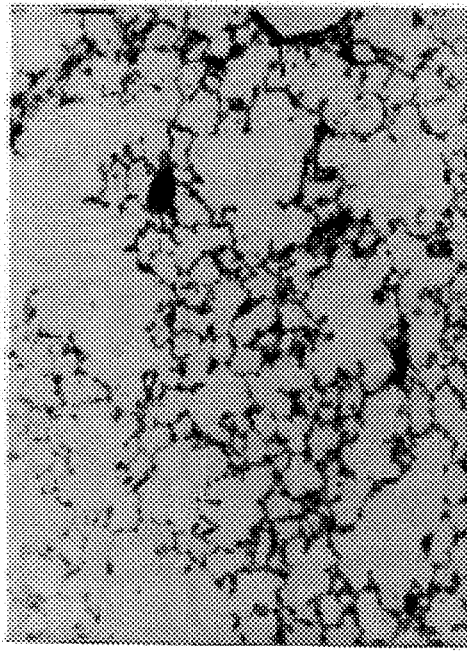
Figure 2D:
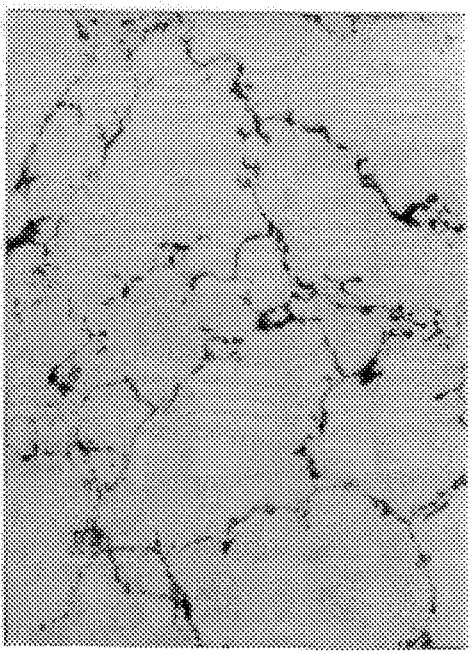
Figure 2A:
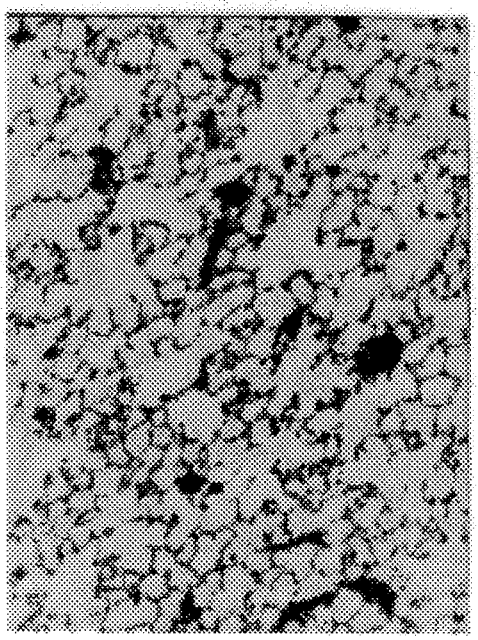
Figure 2C:
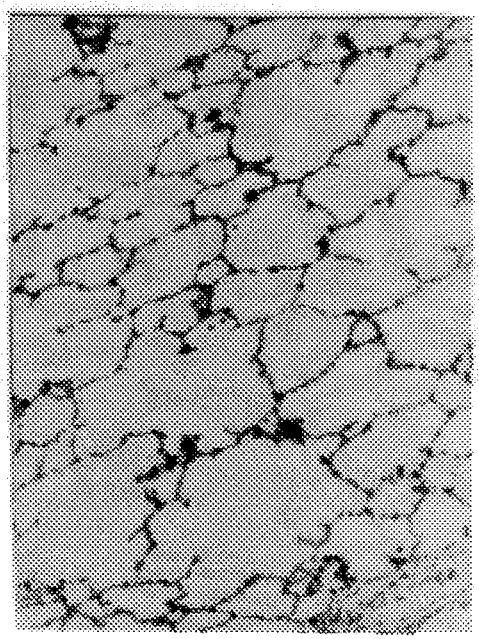

FIGS. 2A, 2B, 2C and 2D:

Photomicrographs of lungs from each treatment group, 1 week following completion of enzyme instillments. FIG. 2A, Hamster lung receiving saline alone. FIG. 2B, Hamster lung instilled with elastase, then hyaluronidase. FIG. 2C, Hamster lung instilled with saline, then elastase. FIG. 2D, Hamster lung instilled with hyaluronidase, then elastase. Note the absence of inflammation in all of the lungs. Original magnification of each photomicrograph: 40×.

FIG. 3:

Twenty-four hours after completion of enzyme instillments, all animals receiving elastase showed a significant reduction in lung elastin content (p<0.05) compared to combined 24 and 48 hour controls receiving saline alone. Pre-treatment of the lung with hyaluronidase did not result in a greater loss of elastin than that observed in the elastase/hyaluronidase and Saline/elastase groups. (N=4 for each group).

FIG. 4:

Intratracheal instillment of hyaluronic acid immediately following elastase administration significantly reduced the amount of air-space enlargement observed at 1 week (p=0.005).

FIG. 5:

Hyaluronic acid enhanced, rather than inhibited, pancreatic elastase activity, as measured by the release of radioactivity from $^3$H-elastin. This effect was observed by the release of radioactivity from $^3$H-elastin. (N-2 for each group).

DETAILED DESCRIPTION OF THE INVENTION

The subject invention is directed to the treatment of respiratory disorders by intratracheal administration of an effective amount of hyaluronic acid. Respiratory disorders include emphysema, chronic bronchitis, asthma, pulmonary edema, acute respiratory distress syndrome, bronchopulmonary dysplasia, pulmonary fibrosis, and pulmonary atelectasis. The treatment is intended for a variety of mammals, such as premature neonates to adult humans.

Administration of hyaluronic acid may be performed by aerosol, which can be generated by a nebulizer, or by instillation. The hyaluronic acid may be administered alone, or with a carrier such as saline solution, DMSO, an alcohol or water. It may be isolated from a natural source such as a bovine or rooster. The effective daily amount of hyaluronic acid is from about 10 µg/kg to about 1 mg/kg of body weight.

The amount of hyaluronic acid intratracheally administered daily may vary from about 10 µg/kg to about 1 mg/kg of body weight of the human being treated. Preferably, the daily amount is from about 10 µg/kg to about 100 µg/kg, for example about 50 µg/kg body weight of the human being treated (daily). The intratracheal hyaluronic acid may be administered in any other of the methods well known to those skilled in the art. For example, the hyaluronic acid may be administered in the form of an aerosol or may be administered by instillation. If administered in the form of an aerosol, a nebulizer is used to produce hyaluronic acid in aerosol form (See for example U.S. Pat. Nos. 4,649,911 and 4,119,096).

Typically, the hyaluronic acid is administered in a pharmaceutically acceptable carrier, such examples include saline solution, DMSO, an alcohol or water. Such carriers are well known in the art, and the specific carriers employed may be varied depending upon factors such as size of the subject being treated, treatment dose and the like.

Further, the time over which the hyaluronic acid is administered may vary as is well known in the art to achieve the desired results. For example, the hyaluronic acid may be administered as an aerosol from about 10 minutes to about 1 hour per treatment regimen, three times daily or until the desired daily dosage is fully administered.

In addition, forms of hyaluronic acid may be derived from bovine sources, rooster comb, human umbilical cord, or streptoccus zoepidicus (See U.S. Pat. Nos. 4,780,414 and 4,784,990). All forms of hyaluronic acid, regardless of source, would follow a treatment similar to that described above.

EXPERIMENTAL DETAILS

The current study examined how lung hyaluronic acid content influences air-space enlargement in elastase-induced emphysema. To determine the effect of a decrease in hyaluronic acid, hamsters received a single intratracheal instillment of hyaluronidase 24 hours prior to administration of pancreatic elastase by the same route. One week later, these animals showed significantly greater air-space enlargement than controls sequentially instilled with saline and elastase (128 vs 100 um; $p<0.05$). Conversely, intratracheal administration of hyaluronic acid immediately after elastase instillment resulted in a marked decrease in air-space enlargement at 1 week compared to controls receiving elastase followed by saline (82 vs 122 um; $p<0.05$). Since hyaluronic acid has no elastase inhibitory capacity, its effect may involve extracellular matrix interactions not directly related to elastic fiber breakdown. This concept is supported by the finding that animals treated with hyaluronidase and elastase showed no greater loss of lung elastin than that observed in the saline/elastase control group, despite demonstrating a marked increase in air-space enlargement. Further work will determine how hyaluronic acid influences air-space enlargement and will evaluate the potential use of this substance as a treatment for emphysema.

METHODS

General Experimental Plan

To determine the effects of hyaluronidase on elastase-induced emphysema, Syrian hamsters received intratracheal instillments of bovine testicular hyaluronidase and, 24 hours later, porcine pancreatic elastase. Controls received: 1) saline followed by elastase, 2) elastase followed by hyaluronidase, and 3) saline followed by saline. Air-space enlargement was measured one week later, using the mean linear intercept method (8). Changes in lung elastin content were determined at 24 and 48 hours by quantifying elastin-specific desmosine and isodesmosine cross-links. The effect of hyaluronidase on lung glycosaminoglycans was not measured in this study, since it was previously shown that an identical dose of the enzyme markedly reduced their content within 24 hours (7). Furthermore, the hyaluronidase preparation was found to contain no elastase activity, as demonstrated by incubation with $^3$H-elastin (7).

To test the possibility that addition of hyaluronic acid may inhibit air-space enlargement, Syrian hamsters were instilled with elastase intratracheally, then immediately given 1 mg of bovine tracheal hyaluronic acid by the same route. Controls received elastase followed by saline alone. Changes in air-space size were evaluated one week later, using the mean linear intercept method (8). To determine whether hyaluronic acid has elastase inhibitory capacity, it was incubated with pancreatic elastase in the presence of $^3$H-elastin. Controls contained elastase and $^3$H-elastin alone.

Hyaluronidase-Elastase Model

Female Syrian hamsters, weighing approximately 100 gms each, were anesthetized by intramuscular injection of ketamine hydrochloride (10 mg in 0.1 ml). The animals were then placed on a rodent surgical table (Harvard Bioscience, South Natick, Mass.) and restrained with elastic bands. The neck fur was shaved with a scalpel and a 2-cm vertical incision was made through the skin and subcutaneous fat. The underlying muscle was then cut to expose the trachea. A 26-gauge needle mounted on a 1-ml syringe was placed inside the tracheal lumen and 900 unite of highly purified bovine testicular hyaluronidase (Sigma Chemical Co., St. Louis, Mo.), dissolved in 0.3 ml normal saline solution, were delivered to the lungs in small increments. Twenty-four hours later, 20 units of porcine pancreatic elastase (Elastin Products, Pacific, Mo.), dissolved in 0.2 ml saline solution, were instilled by the same method. The incision was then closed with several sutures.

Hyaluronic Acid-Elastase Model

Following intratracheal administration of 20 units of pancreatic elastase (see above procedure), hamsters immediately received, by the same route, 1 mg of bovine tracheal hyaluronic acid (Sigma Chemical Co., St. Louis, Mo.), dissolved in 0.2 ml of saline solution.

Mean Linear Intercept Measurements

One week after completion of the enzyme instillments, the hamsters were sacrificed by intraperitoneal injection of chloral hydrate. Their lungs were then fixed in-situ by inserting a catheter into the tracheas and allowing 10% neutral-buffered formalin to inflate the tissues at a pressure of 20 cm $H_2O$. Two hours later, the catheter was removed and the trachea was tied off to minimize deflation. both the lungs and heart were removed from the chest as a single block and additionally fixed in 10% formalin for several days. The lungs were then dissected free of extrapulmonary structures, sectioned randomly, and entirely submitted for histological processing. Slide sections were coded, and mean linear intercept measurements were made by an experienced morphologist (JMC) according to published procedures (8).

Lung Desmosine and Isodesmosine Measurements

Total lung elastin content was determined by measurement of the cross-linking amino acids, desmosine and isodesmosine, according to previously published procedures (7,9). Twenty-four and 48 hours following completion of the enzyme instillments, hamsters were sacrificed by intraperitoneal injection of chloral hydrate. Their lungs were removed from the chest, dissected free of extrapulmonary structured, homogenized, and lyophilized. The dried tissues were then weighed and hydrolyzed in 6N HCl at 110° C. for 18 hours. After evaporation to remove HCl, the samples were reconstituted in water and filtered. Aliquots were spotted on Whatman 3MM and subjected to sequential ascending chromatography, first in butanol, glacial acetic acid, and water (4:1:1), and then in n-propanol, water, and ammonia (134:56:10). Desmosine and isodesmosine, which comigrate, were stained with 1% ninhydrin in acetone, then eluted in 60% propanol and measured for absorbance in a spectrophotometer at 570 nm. The results were normalized using co-chromatographed standards and expressed as micrograms of desmosine and isodesmosine per milligram of dry lung.

Measurement of Elastase Inhibitory Capacity of Hyaluronic Acid

Various amounts of hyaluronic acid (1,10,100 µg) were incubated with pancreatic elastase (1 µg) and $^3$H-elastin in 0.2M Tris buffer, pH 8.0, at 37° C. for 22 hours (7,10). Hyaluronic acid was preincubated with either elastase or $^3$H-elastin for 10 minutes prior to the start of the assay. This was done to allow for the possible binding of one component to another. Following incubation, the samples were filtered, combined with scintillation fluid, and measured for radioactivity. The results were adjusted for nonspecific release of radioactivity and expressed as net counts per minute.

Data Analysis

Differences among the four treatment groups were tested for statistical significance ($p<0.05$) with the Newman-Keuls multiple comparisons test (11). Where only two groups were compared, the two-sample t-test was used.

RESULTS

Pre-treatment with Hyaluronidase: Morphology

Measurements of air-space size, using the mean linear intercept method, were made one week after completion of the enzyme instillments. As shown in FIG. 1, elastase-induced air-space enlargement was markedly enhanced by pre-treatment of the lung with hyaluronidase. Hamsters receiving this enzyme prior to elastase administration had a mean linear intercept value of 128 um, compared to 100 um for those animals initially given saline instead of hyaluronidase. The effect of hyaluronidase was extinguished when the order of administration of the enzymes was reversed. Animals receiving elastase followed by hyaluronidase had a mean linear intercept value of 95.3 um. As previously demonstrated by this laboratory, hyaluronidase, alone, does not cause significant air-space dilation (7).

All treatment groups showed only minimal inflammatory changes at one week, consisting of scattered intraalveolsr clusters of neutrophils and red cells (FIG. 2). No evidence of alveolar epithelial hyperplasia or other interstitial changes were noted.

Pre-treatment with Hyaluronidase: Changes in Elastin

The lung content of elastin-specific desmosine and isodesmosine cross-links was measured 24 and 48 hours following completion of the enzyme instillments. Compared to animals given saline alone, those receiving elastase all showed a significant decrease in cross-linked elastin at 24 hours (FIG. 3). Initial use of hyaluronidase did not produce a greater loss of lung elastin that observed in the saline/elastase or elastase/hyaluronidase treatment groups (206 vs 192 and 184 µg/mg dry lung, respectively). This finding indicates that the additional air-space enlargement seen in the hyaluronidase/elastase group may involve mechanisms unrelated to elastin breakdown.

By 48 hours, lung elastin content was close to normal in all of the elastase-treated groups, reflecting the rapid repair of elastic fibers. The small increase in lung elastin content which occurs in the saline/saline group between 24 and 48 hours may indicate that at least some injury to elastic fibers simply results from instillment of foreign material. It has previously been shown that intratracheal administration of saline induces lung inflammation, which presumably causes nonspecific injury to elastic fibers (6).

Treatment with Hyaluronic Acid: Morphology

Figure 4:
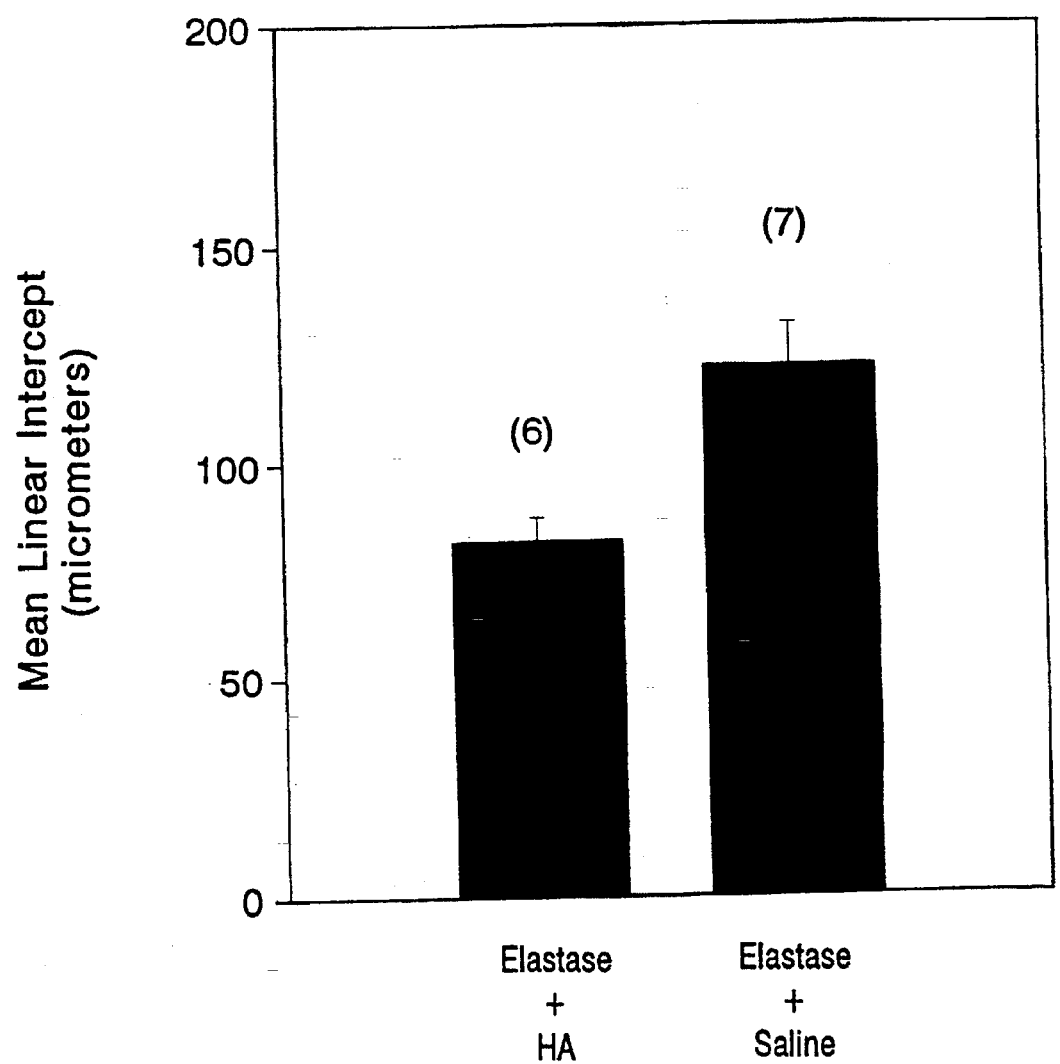

Measurements of air-space size were performed once a week after intratracheal instillments of elastase and hyaluronic acid or elastase and saline. As shown in FIG. 4, animals given hyaluronic acid immediately following elastase administration showed a marked reduction in air-space enlargement compared to those secondarily receiving saline (82 vs 122 um). The additional instillment of saline resulted in greater air-space enlargement than that observed with elastase alone. This may possibly be due to flushing of the elastase into smaller airways.

Histological examination of the lungs from both treatment groups showed minimal inflammatory changes composed of scattered intraalveolar collections of neutrophils and red blood cells. No specific changes were associated with the added administration of hyaluronic acid.

Effect of Hyaluronic Acid on Elastase Activity

Incubation of hyaluronic acid with pancreatic elastase did not reduce $^3$H-elastin breakdown, but instead caused a marked increase in the release of radioactivity from the substrate (FIG. 5). This stimulatory effect was observed regardless of whether hyaluronic acid was preincubated with elastase or $^3$H-elastin and may result from greater interaction between enzyme and substrate (possibly due to alteration of electrostatic bonding).

DISCUSSION

Hyaluronic acid, a high molecular weight polymer composed of repeating saccharide units, plays an important role in stabilizing proteoglycans in the extracellular matrix (12, 13). A number of studies indicate that it also contributes significantly to tissue growth and repair (14,13). In particular, hyaluronic acid has been shown to be a critical component in amphibian limb regeneration, strongly influencing the initial stages of the process (14). One of the main functions of hyaluronic acid may be to reduce cellular cohesion, thereby facilitating the restructuring of tissues.

Production of hyaluric acid is also greatly elevated following experimental induction of both emphysema and interstitial fibrosis (16,18). In both diseases, the increases in this matrix component occur shortly after initiation of lung injury. Among the factors which may stimulate hyaluric acid synthesis is cell regeneration. The damage to alveolar lining cells which occurs in experimental models of interstitial fibrosis results in marked epithelial (type II cell) hyperplasia (19). Hyaluronic acid may facilitate this process by reducing cohesion among the rapidly proliferating cells.

The role of hyaluronic acid in emphysema is less clear. Cellular hyperplasia is not a characteristic of this disease and little tissue remodeling occurs. The ability of hyaluronic acid to reduce air-space size in elastase-induced emphysema may therefore depend more on its interactions with other matrix components than on its capacity to enhance tissue growth.

In a previous study from this laboratory, in which hyaluronidase was found to synergistically interact with 50% oxygen to produce air-space enlargement, it was hypothesized that hyaluronic acid and other glycosaminoglycans may form a meshwork which protects elastic fibers (7). Degradation of these matrix constituents could then be viewed as a means by which elastases and cells, such as monocytes or neutrophils, might gain access to elastic fibers (20).

Despite the attractiveness of this hypothesis, the current findings argue against a direct relationship between hyaluronic acid and elastin breakdown. Pre-treatment with hyaluronidase does not significantly modify elastase-induced breakdown or resynthesis of elastin. Furthermore, hyaluronic acid does not prevent elastin from being degraded by elastase in-vitro. The profound effects exhibited by hyaluronic acid on air-space size may therefore be related to other properties of the molecule.

One particular characteristic of hyaluronic acid which may influence air-space enlargement is its ability to retain water. Negatively charged carboxyl groups attached to the saccharide moieties repel one another, expanding the domain of hyaluronic acid and enhancing its ability to entrap water (15). It has been shown that a loss of hyaluronic acid can reduce extravascular water content in the lung interstitium (21).

With regard to elastic fibers, which contain alternating hydrophilic and hydrophobic domains, adequate hydration of the surrounding matrix may be required for maintenance of normal tissue recoil (22). Concomitant loss of hyaluronic acid during elastic fiber breakdown could increase interference with lung mechanics, resulting in a greater degree of air-space dilation and rupture. Conversely, addition of hyaluronic acid to the lung may allow damaged elastic fibers to retain their recoil properties, thereby reducing lung injury.

The potential therapeutic value of hyaluronic acid will depend on demonstrating its effectiveness under a variety of experimental conditions. In particular, it will be necessary to determine whether hyaluronic acid can limit air-space enlargement when delivered at intervals both before and after instillment of pancreatic elastase into the lung. Additional studies will be required to assess the efficacy of hyaluronic acid against neutrophil elastase, since this enzyme is thought to play a major role in human emphysema.

It should be emphasized that no single form of treatment of emphysema may prove entirely successful. If the disease represents a general response of the lung to a variety of insults, then halting its progression may require the development of multiple therapeutic agents, whose effectiveness may vary according to the nature of the underlying lung injury.

REFERENCES

REFERENCES

1. Janoff A., Elastases and emphysema: Current assessment of the protease-antiprotease hypotheses. Am. Rev. Respir. Dis. 132:417–433, 1985.
2. Senior RM, Kuhn C III: The pathogenesis of emphysema. In Fishman AP (ed), Pulmonary Diseases and Disorders, 2d ed, New York, McGraw-Hill, pp. 1209–1218, 1988.
3. Bruce MC: The extracellular matrix of the lung: Implications in COPD. In Cherniack NS (ed), Chronic Obstructive Pulmonary Disease, Philadelphia, W. B. Saunders, pp. 29–44, 1991.
4. Zimmerman M, Powers JC: Design and properties of synthetic elastase inhibitors. in Elastin and Elastases, vol II, Robert L. Horsebeck W (eds), Boca Raton, CRC Press, pp. 109–123, 1989.
5. Laurell C-B, Eriksson S: The electrophoretic alpha$_1$-globulin pattern of serum in alpha$_1$-entropion deficiency. Scand. J. Olin. Lab. Invest. 15:132–140, 1993.
6. Cantor JO, Keller S, Cerretta JM, Manahan J, Evans HE, Turino GM: The effect of 50% oxygen on air-space enlargement and cross-linked elastin syntheses in hamsters with elastase-induced emphysema. Amer. Rev. Respir. Dis. 142:668–673, 1990.
7. Cantor JO, Cerreta, JM, Armand G, Keller S, Turino GM: Pulmonary air-space enlargement induced by intratracheal instillment of hyaluronidase and concomitant exposure to 60% oxygen. Exper. Lung Res. 19:177–192, 1993.
8. Dunnill MS: Quantitative methods in the study of pulmonary pathology. Thorax 17:328–8, 1962.
9. Keller S, Ghosh AK, Ghosh AK, Turino GM, Mandl I: Separationof the cross-linking amino acids of elastin on thin-layer plates. J. Chromat. 305:451–464, 1984
10. Stone PJ, Crombie G, Franzblau G: The use of tritiated elastin for the determination of subnanogram amounts of elastase. Anal. Biochem. 80:572–577, 1971.
11. Winer BJ: Statistical Principles in Experimental Design (ed 2). New York, McGraw-Hill, 1971.
12. Rosenberg LC, Varma R: An overview of proteoglycans in physiology and pathology. In Varma Rs, Varma R (eds), Glycosaminoglycans and Proteoglycans in Physiological and Pathological Processes of Body systems. Basel, Karger, pp. 1–4, 1982.
13. Heinegard D, Paulsson M: Structure and metabolism of proteoglycans. In Pitz KA, Reddi Ah (eds), Etracellular Matrix Biochemistry. New York, Elsevier, pp. 277–328, 1984.
14. Toole BP, Gross: The extracellular matrix of the regenerating newt limb: Synthesis and removal of hyaluronate prior to differentiation. Dev. Biol. 25:57–77, 1971.
15. Toole BF: Glycosaminoglycans in morphogenesis: In Hay ED (ed), Cell Biology of Extracellular Matrix. New York, Plenum Press, pp. 259–294, 1981.
16. Lafuma C, Moczar M, Lange F, Robert L: Biosynthesis of hyaluronic acid, heparan sulfaim and structural glycoproteins in hamster lung explants during elastase induced emphysema. Connect. Tissue Res. 13:169–179, 1985.
17. Karlinsky JB: Glycosaminoglycans in emphysematous and fibrotic hamster lungs. Am. Rev. Respir. Dis. 125:85–88, 1982.
18. Bray BA, Sampson PM, Osman M, Giandomenico, Turino GM: Early changes in lung tissue hyaluronan (hyaluronic acid) and hyaluronidase in bleomycin-induced alveolitis in hamsters. Am. Rev. Respir. Dis. 143:284–288, 1991.
19. Cantor JO: Bleomycin-induced pulmonary fibrosis. In Cantor JO (ed), Handbook of animal Models of Pulmonary Disease, vol I Boca Raton, CRC Press, pp. 117–129, 1989.
20. Campbell EJ, Senior RM, McDonald JA, Cox DL: Proteolysis by neutrophils: Relative importance of cell-substrate contact and inactivation of proteinase inhibitors in vitro. J. Olin. Invest. 70:845–852, 1982.
21. Rosenbloom J, Bashir M, Yeh H, Rosenbloom J, Ornstein-Goldstein N, Fazio M, Kahari V-M, Vitto J: Regulation of elastin gene expression. In Weinbaum G, Giles RE, Krell BD (eds), Pulmonary Emphysema: The Rationale for Therapeutic Intervention. New York, Ny Acad Sci, pp. 116–135, 1991

What is claimed is:

1. A method of treating a respiratory disorder, wherein the respiratory disorder is selected from the consisting of emphysema, chronic bronchitis, asthma, pulmonary edema, acute respiratory distress syndrome, bronchopulmonary dysplasia, pulmonary fibrosis, and pulmonary atelectasis, which comprises intratracheally administering to a mammal an effective amount of a hyaluronic acid so as to treat the respiratory disorder.

2. A method of claim 1, wherein the intratracheal administration is performed by instillation.

3. A method of claim 1, wherein the intratracheal administration is performed by aerosol.

4. A method of claim 3, wherein the aerosol is generated by a nebulizer.

5. A method of claim 1, wherein the mammal is a human.

6. A method of claim 1, wherein the mammal is a human adult.

7. A method of claim 1, wherein the mammal is a human neonate.

8. A method of claim 7, wherein the neonate is premature.

9. A method of claim 1, wherein the amount of a hyaluronic acid is administered with a carrier.

10. A method of claim 9, wherein the carrier is saline solution, DMSO, an alcohol or water.

11. A method of claim 1, wherein the effective amount of hyaluronic acid is from about 10 µg/kg to about 1 mg/kg/day.

12. A method of claim 1, wherein the hyaluronic acid is isolated from a natural source.

13. A method of claim 12, wherein the natural source is bovine or rooster.

14. A method of claim 1, wherein the hyaluronic acid is prepared by a bioprocess such as fermentation.

* * * * *